US012799123B2

(12) United States Patent
Guo et al.

(10) Patent No.: US 12,799,123 B2
(45) Date of Patent: Nov. 17, 2026

(54) PYRAZOLOPYRIMIDINE ESTER COMPOUND

(71) Applicant: Shanghai Maius Pharmaceutical Co. Ltd., Shanghai (CN)

(72) Inventors: Yekun Guo, Shanghai (CN); Dujian Huang, Shanghai (CN); Xiang Hu, Shanghai (CN); Mingfeng Shi, Shanghai (CN)

(73) Assignee: Shanghai Maius Pharmaceutical Co. Ltd., Shanghai (CN)

( * ) Notice: Subject to any disclaimer, the term of this patent is extended or adjusted under 35 U.S.C. 154(b) by 379 days.

(21) Appl. No.: 18/687,437

(22) PCT Filed: Jun. 9, 2022

(86) PCT No.: PCT/CN2022/097873
§ 371 (c)(1),
(2) Date: Feb. 28, 2024

(87) PCT Pub. No.: WO2023/045411
PCT Pub. Date: Mar. 30, 2023

(65) Prior Publication Data

US 2024/0360144 A1 Oct. 31, 2024

(30) Foreign Application Priority Data

Sep. 26, 2021 (CN) .......................... 202111131059.0

(51) Int. Cl.
*C07D 487/04* (2006.01)
*A61K 31/519* (2006.01)

(52) U.S. Cl.
CPC .......... *C07D 487/04* (2013.01); *A61K 31/519* (2013.01)

(58) Field of Classification Search
CPC ............................ C07D 487/04; A61K 31/519
USPC ....................................................... 514/262.1
See application file for complete search history.

(56) References Cited

FOREIGN PATENT DOCUMENTS

| | | | |
|---|---|---|---|
| CN | 106478633 | A | 3/2017 |
| WO | 2016/204991 | A1 | 12/2016 |
| WO | 2017/039425 | A1 | 3/2017 |
| WO | 2020/176868 | A1 | 9/2020 |

OTHER PUBLICATIONS

English translation of CN 106478633 A1, published on Mar. 8, 2017; translation obtained on Mar. 10, 2026 (Year: 2017).*

* cited by examiner

*Primary Examiner* — Kristin A Vajda
(74) *Attorney, Agent, or Firm* — RABIN & BERDO, P.C.

(57) ABSTRACT

The present invention provides a pyrazolopyrimidine ester compound of the following general structural formula:

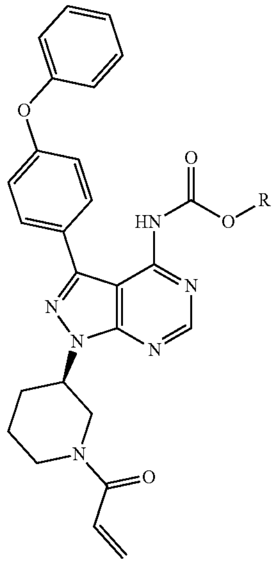

The present invention also provides a method of preparing the pyrazolopyrimidine ester compound and use thereof for preparation of a drug for treating blood disease such as lymphoma and lymphocytic leukemia. The pyrazolopyrimidine ester compound of the present invention undergoes a mild first-pass effect, and once orally absorbed, can rapidly enter the blood plasma to deliver the intended therapeutic effect. It produces a flat plasma drug concentration peak, but has a great AUC. It can provide high bioavailability, a steady plasma drug concentration profile and a sustained duration of action. Compared with the existing BTK inhibitors, it can better address clinical needs.

5 Claims, 3 Drawing Sheets

PYRAZOLOPYRIMIDINE ESTER COMPOUND

TECHNICAL FIELD

The present invention pertains to the field of medicine, and particularly relates to a pyrazolopyrimidine ester compound.

BACKGROUND

Lymphoma is blood cancer that develops from lymphocytes, which are a subtype of blood cells produced in the bone marrow and found in the blood and lymphatic tissue. Hodgkin's lymphoma (HL) and non-Hodgkin's lymphoma (NHL) are two main types of lymphoma, with the latter accounting for 80% to 90% of total lymphoma cases. NHL includes a group of heterogeneous malignant tumors that originate from the lymphatic tissue, and the most common subtypes of NHL in China are diffuse large B-cell lymphoma (DLBCL), chronic lymphocytic leukemia/small lymphocytic lymphoma (CLL/SLL), follicular lymphoma (FL), marginal zone B cell lymphoma (MZL) and mantle cell lymphoma (MCL). Depending on the origin of lymphocytes, about 85% of these cases are B-cell lymphoma.

Bruton's tyrosine kinase (BTK) is a non-receptor cytoplasmic tyrosine protein kinase of the Tec family. BTK is involved in the transduction of TLR, BAFF-R, BCR and CXCR4/5 signals, as well as in the proliferation, differentiation, apoptosis and migration of regulatory B-cells. As BTK plays a crucial role in pathogenesis of malignant B-cell lymphoma, BTK inhibitors are being used as important drugs for B-cell lymphoma treatment.

At present, a number of BTK inhibitors have been explicitly proven in clinical trials to have superior efficacy over the traditional chemotherapy, against malignant B-cell lymphoma, the most highly prevalent lymphoma. BTK inhibitors currently available on the market include ibrutinib, acalabrutinib, zanubrutinib, tirabrutinib, orelabrutinib, etc. Structural formulas of these are given below:

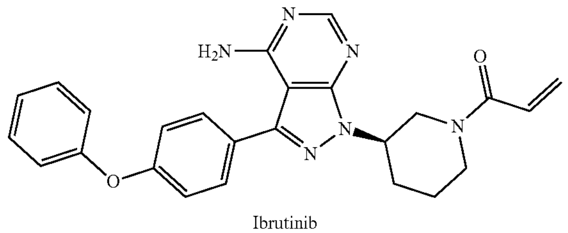

Ibrutinib

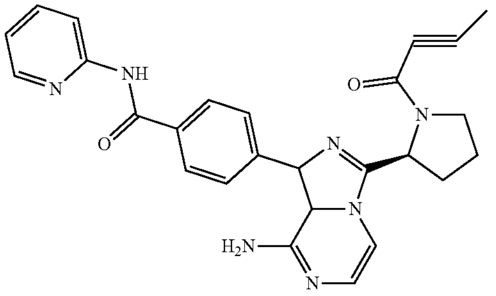

Acalabruntinib

-continued

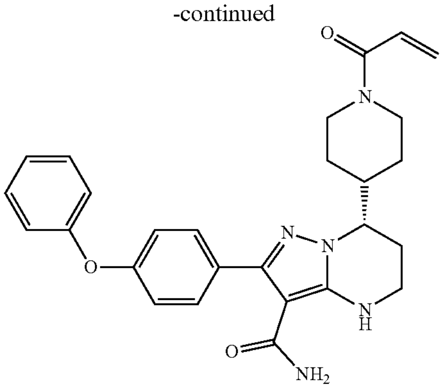

Zanubrutinib

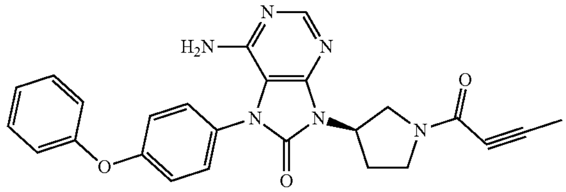

Tirabrutinib

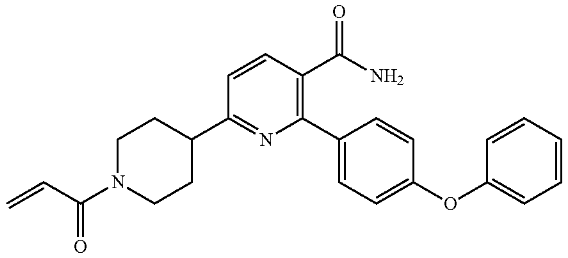

Orelabrutinib

Ibrutinib is the first launched BTK inhibitor in the world. It provides an alternative mode of CLL and MCL treatment—treatment by oral administration is made possible, and sustained response can be obtained.

Despite confirmed long-term efficacy, BTK inhibitors are still associated with some disadvantages, such as a significant first-pass effect following oral absorption, which leads to low absolute bioavailability, as well as both a short time to peak plasma concentration and a short elimination half-life, which lead to significant fluctuations in plasma drug concentration.

Once an adverse reaction such as bleeding or bone marrow suppression is noticed during the use of a BTK inhibitor, the dose must be adjusted, or even the treatment must be terminated. Due to fast absorption and elimination and large fluctuations in plasma drug concentration, a high plasma drug concentration peak becomes a limiting factor in the dose at which a BTK inhibitor can be used, which directly affects the efficacy of the drug.

SUMMARY

In view of the above-described disadvantages and deficiencies in practical use of BTK inhibitors, the inventors have attempted a variety of structural modifications to existing BTK inhibitors and successfully identified a class of pyrazolopyrimidine ester compounds from the modified compounds based on pharmacokinetic and other studies thereof.

Accordingly, in a first aspect of the present invention, there is provided a pyrazolopyrimidine ester compound of general structural formula (I):

(I)

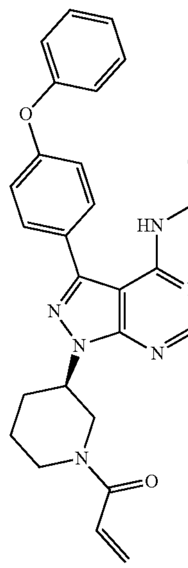

where R is selected from $—C_2H_5$, $—CH(CH_3)_2$, $—(CH_2)_2CH_3$, $—(CH_2)_3CH_3$, $—CH_2CH(CH_3)_2$, $—(CH_2)_5CH_3$, —Bn, $—(CH_2)_{10}CH_3$, $—(CH_2)_{13}CH_3$, $—CH(C_2H_5)_2$, $—CH(CH(CH_3)_2)_2$, $—(CH_2)_7CH_3$ and $—CH_2CH(C_2H_5)_2$.

In a second aspect of the present invention, there is provided a method of preparation of the pyrazolopyrimidine ester compound, in which commercially available 1-[(3R)-3-[4-amino-3-(4-phenoxyphenyl)-1H-pyrazolo[3,4-D]pyrimidin-1-yl]-1-piperidinyl]-2-propen-1-one is taken as a starting material and reacts with a corresponding chloroformate to produce a target compound, according to:

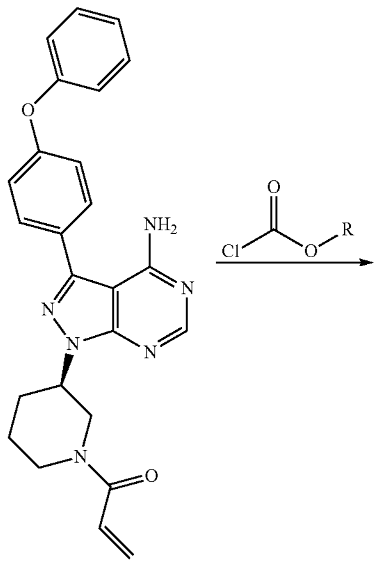

-continued

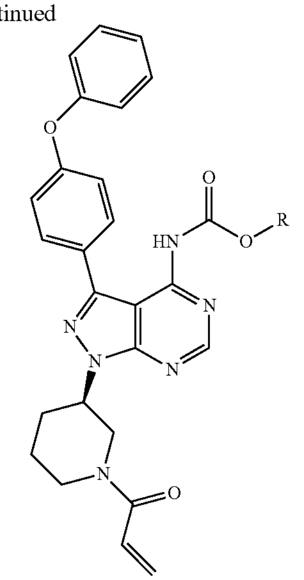

where R is selected from $—C_2H_5$, $—CH(CH_3)_2$, $—(CH_2)_2CH_3$, $—(CH_2)_3CH_3$, $—CH_2CH(CH_3)_2$, $—(CH_2)_5CH_3$, —Bn, $—(CH_2)_{10}CH_3$, $—(CH_2)_{13}CH_3$, $—CH(C_2H_5)_2$, $—CH(CH(CH_3)_2)_2$, $—(CH_2)_7CH_3$ and $—CH_2CH(C_2H_5)_2$.

Further, the method of preparation of the pyrazolopyrimidine ester compound may include the steps of adding the starting material 1-[(3R)-3-[4-amino-3-(4-phenoxyphenyl)-1H-pyrazolo[3,4-D]pyrimidin-1-yl]-1-piperidinyl]-2-propen-1-one, the chloroformate and a solvent to a reactor; and after the starting material and the chloroformate are dissolved in the solvent, adding a base to trigger the reaction.

Alternatively, the method of preparation of the pyrazolopyrimidine ester compound may include the steps of:

adding the starting material 1-[(3R)-3-[4-amino-3-(4-phenoxyphenyl)-1H-pyrazolo[3,4-D]pyrimidin-1-yl]-1-piperidinyl]-2-propen-1-one, a solvent and a base to a reactor; and after the starting material and the base are dissolved in the solvent, adding the chloroformate to trigger the reaction, wherein with the starting material being taken as a reference, the base is added at an amount of 6.0±0.5 eq. and the chloroformate is added at an amount of 2.0±0.5 eq., and wherein the chloroformate is added, after being dissolved in the solvent, at 0-10° C. to trigger the reaction.

Further, after the reaction is complete, the pyrazolopyrimidine ester compound may be obtained by post-reaction processing including separation and purification.

In a third aspect of the present invention, there is provided use of the pyrazolopyrimidine ester compound for preparation of a drug for treating blood disease such as lymphoma and lymphocytic leukemia.

The present invention has the benefits as follows:

1. The pyrazolopyrimidine ester compound of the present invention undergoes a mild first-pass effect. Once orally absorbed, it rapidly enters the blood plasma and is hydrolyzed into the active metabolite 1-[(3R)-3-[4-amino-3-(4-phenoxyphenyl)-1H-pyrazolo[3,4-D]pyrimidin-1-yl]-1-piperidinyl]-2-propen-1-one, also known as the 4-amino active metabolite (4-AAM), which can exert the intended therapeutic effect. 4-AAM has been commonly recognized in the current clinical practice as an active substance.

Due to different behavior in absorption and metabolism, the compound of the present invention produces a lower plasma drug concentration peak and has a greater AUC, compared with 4-AAM. Its pharmacokinetic properties make it more suitable to address clinical needs than the existing BTK inhibitors. Compound 3 is hydrolyzed at the highest rate in the blood plasma, and the resulting 4-AAM has the highest AUC, which is much higher than that of Compound 3 itself.

2. The AUC of the pyrazolopyrimidine ester compound of the present invention is 77%-180% of that of 4-AAM administered at the same molar amount. Moreover, it has a time to peak concentration of up to 2 h and a mean retention time of as long as 2.5-4.3 h, both significantly advantageous over those of 4-AAM.

Compound 3 is hydrolyzed at the highest rate, and the resulting 4-AAM has both a greater AUC and a higher plasma drug concentration than Compound 3 itself. The AUC is 180% of that of 4-AAM directly administered at the same molar amount. Its time to peak concentration is 2 h, and its mean retention time is 2.9 h. Compound 1 has an AUC, which is 1$^{37}$% of that of 4-AAM administered at the same molar amount, a time to peak concentration of 1 h and a mean retention time of 2.8 h. Compound 4 has an AUC, which is 127% of that of 4-AAM administered at the same molar amount, a time to peak concentration of 2 h and a mean retention time of 2.5 h. Compound 2 has an AUC, which is 88% of that of 4-AAM administered at the same molar amount, a time to peak concentration of 2 h and a mean retention time of 4.3 h.

3. The pyrazolopyrimidine ester compound of the present invention can provide higher bioavailability, a more steady plasma drug concentration profile and a longer duration of action.

DETAILED DESCRIPTION

Figure 1:
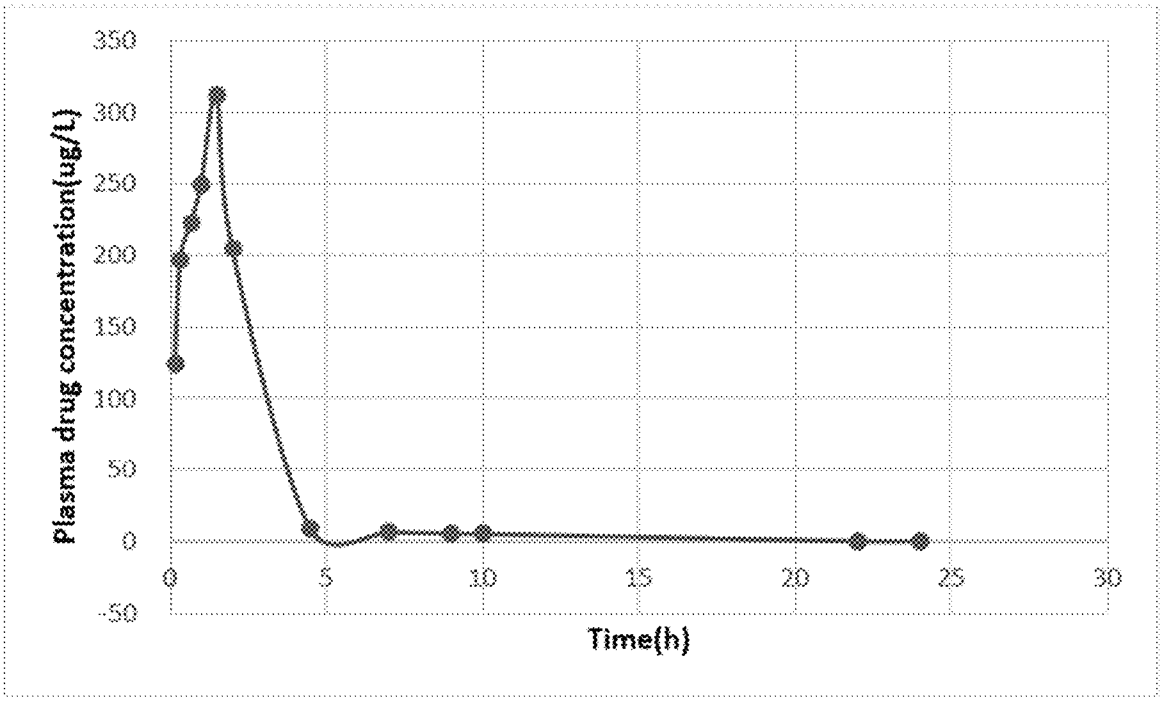
FIG. 1 shows a Plasma drug concentration-time curve of 4-AAM after it is oral gavage administered to rats.

The present invention will be described clearly and fully below with reference to specific embodiments thereof and to the accompanying drawings. It is understood that the embodiments set forth herein are merely some, but not all, of the possible embodiments of this invention. Any and all other embodiments devisable by skilled artisans in light of the disclosed embodiments without paying any creative effort are considered to fall within the scope of the invention.

The following are the definitions of some terms as used in the context of the present invention.

The term "plasma drug concentration" refers to the total concentration of a drug in the blood plasma after it is absorbed in the form of being either bound to plasma protein or free in the plasma. Sometimes, this term refers to the concentration of a drug in the whole blood. The potency of a drug is proportional to its plasma concentration, and its in vivo concentration varies over time.

The term "time to peak concentration" refers to the time that it takes for a drug to reach its peak plasma drug concentration after its administration. At the end of this time, the drug is present at a maximum plasma drug concentration. The time to peak concentration of a drug can be used to analytically determine a suitable time for the drug to be taken.

The term "AUC" stands for the area under the curve of the plasma drug concentration of a drug as a function of time. In modern pharmacokinetic studies, AUC is an important parameter for assessing the in vivo properties of a drug. This area represents the total amount of absorption of a drug within a certain time after it is administered for a single time and can be used to calculate the drug's bioavailability.

The term "elimination half-life" refers to the time that it takes for the plasma drug concentration of a drug that has reached a distribution equilibrium to drop by 50%.

The term "first-pass effect" refers to metabolism of an oral drug administered through the gastrointestinal tract in the intestinal mucosa and liver before it is absorbed and enters the blood circulation, which leads to a reduction in the amount of the parent drug that enters blood circulation.

In the context of the present invention, some compounds of general structural formula (I) that it is directed to, as well as the respective R groups therein, are numbered as shown in Table 1.

TABLE 1

| Compound No. | R Group |
|---|---|
| 1 | $—CH(CH_3)_2$ |
| 2 | $—(CH_2)_2CH_3$ |
| 3 | $—(CH_2)_3CH_3$ |
| 4 | $—CH_2CH(CH_3)_2$ |
| 5 | $—(CH_2)_5CH_3$ |
| 6 | —Bn |
| 7 | $—(CH_2)_{10}CH_3$ |
| 8 | $—(CH_2)_{13}CH_3$ |
| 9 | $—CH(C_2H_5)_2$ |
| 10 | $—CH(CH(CH_3)_2)_2$ |
| 11 | $—(CH_2)_7CH_3$ |
| 12 | $—C_2H_5$ |
| 13 | $—CH_2CH(C_2H_5)_2$ |

Example 1 Preparation of Compound 1

Under the protection of nitrogen, to a 500-ml three-neck flask, 10 g of a substrate (1-[(3R)-3-[4-amino-3-(4-phenoxyphenyl)-1H-pyrazolo[3,4-D]pyrimidin-1-yl]-1-piperidinyl]-2-propen-1-one), 200 g of a solvent (dichloromethane) and 10 g of isopropyl chloroformate were added. After the substrate and isopropyl chloroformate were dissolved in the solvent, the temperature was cooled to 10° C., and 6.45 g of a base (pyridine) was added dropwise within 10-20 minutes. The temperature was kept, and the reaction was run 3-4 hours. The reaction was terminated when TLC monitoring showed almost complete consumption of the starting materials.

100 g of ice water was added, followed by separation of the aqueous and organic phases. The aqueous phase was extracted with 50 g of dichloromethane. The organic phases were combined, washed with water, concentrated and passed through a column. 5.0 g of the product was obtained at a yield of 41.9%.

$^{1}$H NMR (400 MHz, $CDCl_3$) δ 8.78 (s, 1H), 8.33 (s, 1H), 7.76 (d, J=5.6 Hz, 2H), 7.37-7.40 (t, J=5.2 Hz, 2H), 7.15-7.18 (m, 3H), 7.07-7.09 (m, 2H), 6.54-6.65 (m, 1H), 6.27-6.33 (t, J=12 Hz, 1H), 5.66-5.74 (dd, J=25.2, 6.8 Hz, 1H), 4.82-4.86 (m, 1H), 4.01-4.61 (m, 1H), 3.19-3.82 (m, 1H), 2.38-2.46 (m, 1H), 2.27-2.29 (m, 1H), 2.00-2.04 (m, 2H), 1.74-1.76 (m, 1H), 1.20-1.34 (m, 8H).

$^{13}$C NMR (400 MHz, $CDCl_3$) δ 171.19, 165.77, 158.51, 156.46, 155.13, 153.04, 150.88, 144.12, 129.94 (2C), 129.70 (2C), 128.19, 127.81, 127.56, 123.98, 119.43 (2C), 119.03 (2C), 102.16, 70.41, 53.77, 52.75, 49.98, 46.01, 30.13 (2C), 25.31.

As detected by mass spectrometry, [M+H]+=527.3, in consistence with the molecular structural formula.

Example 2 Preparation of Compound 2

The same preparation steps as in Example 1 were performed, except that the isopropyl chloroformate was replaced with propyl chloroformate. 5.5 g of the target product was obtained at a yield of 46.1%.

$^{1}$H NMR (400 MHz, $CDCl_3$) δ 8.77 (s, 1H), 8.26 (s, 1H), 7.60-7.67 (m, 2H), 7.37-7.40 (t, J=5.2 Hz, 2H), 7.15-7.19 (m, 3H), 7.07-7.10 (m, 2H), 6.54-6.65 (m, 1H), 6.27-6.33 (t, J=12 Hz, 1H), 5.66-5.74 (dd, J=26.4, 6.8 Hz, 1H), 4.89-4.91 (m, 1H), 4.04-4.61 (m, 1H), 3.20-3.82 (m, 1H), 2.38-2.45 (m, 1H), 2.27-2.29 (m, 1H), 2.02-2.04 (m, 2H), 1.74-1.76 (m, 1H), 1.52-1.64 (m, 3H), 1.26-1.46 (m, 1H), 0.79-1.04 (m, 4H).

$^{13}$C NMR (400 MHz, $CDCl_3$) δ 165.78, 158.58, 156.45 155.22, 154.74, 152.79, 151.25, 143.97, 129.95 (2C), 129.78 (2C), 128.21, 127.55, 124.01, 119.42 (2C), 119.14, 119.09 (2C), 102.01, 53.79, 52.79, 49.99, 45.92, 42.20, 25.30, 23.88, 14.20.

As detected by mass spectrometry, $[M+H]^+$=527.3, in consistence with the molecular structural formula.

Example 3 Preparation of Compound 3

The same preparation steps as in Example 1 were performed, except that the isopropyl chloroformate was replaced with butyl chloroformate. 5.8 g of the target product was obtained at a yield of 47.3%.

$^{1}$H NMR (400 MHz, $CDCl_3$) δ 8.77 (s, 1H), 8.40 (s, 1H), 7.64-7.66 (m, 2H), 7.38-7.44 (t, J=5.2 Hz, 2H), 7.16-7.19 (m, 3H), 7.08-7.09 (m, 2H), 6.54-6.65 (m, 1H), 6.27-6.33 (t, J=12 Hz, 1H), 5.66-5.74 (dd, J=26.0, 6.4 Hz, 1H), 4.89-4.90 (m, 1H), 4.06-4.61 (m, 1H), 3.19-3.81 (m, 1H), 2.35-2.45 (m, 1H), 2.27-2.29 (m, 1H), 2.01-2.09 (m, 2H), 1.74-1.76 (m, 1H), 1.52-1.60 (m, 3H), 1.14-1.38 (m, 3H), 0.81-0.95 (m, 4H).

$^{13}$C NMR (400 MHz, $CDCl_3$) δ 165.77, 158.64, 156.42, 155.29, 154.74, 152.81, 151.13, 143.84, 129.95 (2C), 129.81 (2C), 128.19, 127.56, 124.02, 119.56, 119.44 (2C), 119.12 (2C), 106.47, 66.20, 53.80, 52.79, 49.98, 45.91, 42.19, 29.99, 25.29, 23.88.

As detected by mass spectrometry, $[M+H]^+$=541.3, in consistence with the molecular structural formula.

Example 4 Preparation of Compound 4

The same preparation steps as in Example 1 were performed, except that the isopropyl chloroformate was replaced with isobutyl chloroformate. 5.2 g of the target product was obtained at a yield of 42.4%.

$^{1}$H NMR (400 MHz, $CDCl_3$) δ 8.78 (s, 1H), 8.06 (s, 1H), 7.76-7.77 (d, J=4.4 Hz, 2H), 7.37-7.40 (t, J=5.2 Hz, 2H), 7.15-7.18 (m, 3H), 7.07-7.09 (m, 2H), 6.54-6.65 (m, 1H), 6.27-6.33 (t, J=12.6 Hz, 1H), 5.66-5.74 (dd, J=26.0, 6.4 Hz, 1H), 4.89-4.91 (m, 1H), 4.04-4.61 (m, 1H), 3.20-3.80 (m, 1H), 2.38-2.45 (m, 2H), 2.27-2.29 (m, 1H), 2.01-2.04 (m, 2H), 1.88-1.92 (m, 2H), 0.76-1.02 (m, 8H).

$^{13}$C NMR (400 MHz, $CDCl_3$) δ 165.78, 158.63, 156.37, 155.32, 154.75, 152.77, 151.07, 143.77, 129.96 (2C), 129.85 (2C), 129.73, 128.21, 127.54, 124.06, 119.40 (2C), 119.06 (2C), 101.72, 72.23, 53.80, 52.79, 49.98, 46.09, 29.99 (2C), 25.29, 23.87.

As detected by mass spectrometry, $[M+H]^+$=541.3, in consistence with the molecular structural formula.

Example 5 Preparation of Compound 5

The same preparation steps as in Example 1 were performed, except that the isopropyl chloroformate was replaced with hexyl chloroformate. 4.8 g of the target product was obtained at a yield of 37.3%.

$^{1}$H NMR (400 MHz, $CDCl_3$) δ 8.77 (s, 1H), 8.11-8.13 (d, J=8.4 Hz, 1H), 7.64-7.67 (m, 2H), 7.37-7.40 (t, J=5.2 Hz, 2H), 7.15-7.18 (m, 3H), 7.07-7.09 (m, 2H), 6.54-6.63 (m, 1H), 6.27-6.33 (t, J=12.8 Hz, 1H), 5.66-5.74 (dd, J=26.0, 6.8 Hz, 1H), 4.89-4.91 (m, 1H), 4.01-4.61 (m, 1H), 3.19-3.81 (m, 1H), 2.35-2.45 (m, 1H), 2.27-2.29 (m, 1H), 2.01-2.03 (m, 2H), 1.74-1.76 (m, 1H), 1.50-1.59 (m, 3H), 1.24-1.37 (m, 7H), 0.84-0.90 (m, 4H).

$^{13}$C NMR (400 MHz, $CDCl_3$) δ 165.79, 158.56, 156.47, 155.27, 154.75, 152.79, 151.19, 143.78, 129.94 (2C), 129.80 (2C), 128.21, 127.54, 124.00, 119.56, 119.37 (2C), 119.14 (2C), 101.93, 66.51, 53.80, 52.79, 49.98, 45.92, 42.20, 32.77, 30.26, 29.98, 23.88, 14.20.

As detected by mass spectrometry, $[M+H]^+$=569.3, in consistence with the molecular structural formula.

Example 6 Preparation of Compound 6

The same preparation steps as in Example 1 were performed, except that the isopropyl chloroformate was replaced with benzyl chloroformate. 6.5 g of the target product was obtained at a yield of 49.9%.

$^{1}$H NMR (400 MHz, $CDCl_3$) δ 8.77 (s, 1H), 7.85 (s, 1H), 7.63-7.65 (m, 2H), 7.34-7.38 (m, 7H), 7.13-7.18 (m, 3H), 7.06-7.07 (d, J=5.6 Hz, 2H), 6.53-6.65 (m, 1H), 6.27-6.33 (t, J=9.2 Hz, 1H), 5.65-5.74 (dd, J=26.8, 6.0 Hz, 1H), 5.10 (s, 2H), 4.88-4.90 (m, 1H), 4.04-4.60 (m, 1H), 3.19-3.80 (m, 1H), 2.36-2.42 (m, 1H), 2.26-2.28 (m, 1H), 2.01-2.03 (m, 1H), 1.70-1.75 (m, 3H).

$^{13}$C NMR (400 MHz, $CDCl_3$) δ 165.77, 158.69, 156.35, 154.72, 152.54, 150.72, 143.62, 135.14, 129.99 (2C), 129.88 (2C), 128.75, 128.65 (2C), 128.58, 128.42 (2C), 128.22, 127.54, 124.09, 124.06, 119.50 (2C), 119.14 (2C), 101.75, 67.87, 53.82, 45.84, 42.19, 30.28, 25.29.

As detected by mass spectrometry, $[M+H]^+$=575.3, in consistence with the molecular structural formula.

Example 7 Preparation of Compound 7

The same preparation steps as in Example 1 were performed, except that the isopropyl chloroformate was replaced with crude n-undecyl chloroformate prepared from 5 eq. of n-undecanol, 7.5 eq. of triethylamine and 2.5 eq. of triphosgene. The reaction was subject to column chromatography, giving 1.38 g of the target compound at a yield of 19.1%.

$^{1}$H NMR (400 MHz, DMSO-$d_6$) δ 11.48 (s, 1H), 8.84 (d, J=10.4 Hz, 1H), 7.82 (d, J=8.3 Hz, 2H), 7.42-7.37 (m, 2H), 7.15 (t, J=7.4 Hz, 1H), 7.10 (d, J=8.7 Hz, 2H), 7.07-7.03 (m, 2H), 6.76 (ddd, J=39.6, 16.3, 10.5 Hz, 1H), 6.07 (t, J=15.7 Hz, 1H), 5.63 (dd, J=32.5, 10.3 Hz, 1H), 4.45-4.01 (m, 5H), 2.13-1.98 (m, 2H), 1.86 (d, J=11.1 Hz, 1H), 1.58 (dd, J=13.6, 6.6 Hz, 2H), 1.43 (s, 1H), 1.24 (dd, J=24.6, 8.0 Hz, 18H), 0.81 (dd, J=9.0, 4.6 Hz, 3H).

As detected by mass spectrometry, $[M+H]^+$=639.39, in consistence with the molecular structural formula.

Example 8 Preparation of Compound 8

The same preparation steps as in Example 1 were performed, except that the isopropyl chloroformate was replaced with crude n-tetradecyl chloroformate prepared from 5 eq. of n-tetradecanol, 7.5 eq. of triethylamine and 2.5 eq. of triphosgene. The reaction was subject to column chromatography, giving 1.35 g of the target compound at a yield of 17.5%.

$^1$H NMR (600 MHz, DMSO-$d_6$) δ 11.47 (s, 1H), 8.88-8.77 (m, 1H), 7.81 (d, J=7.8 Hz, 2H), 7.40-7.36 (m, 2H), 7.14 (t, J=7.4 Hz, 1H), 7.11-7.05 (m, 2H), 7.05-7.01 (m, 2H), 6.82-6.67 (m, 1H), 6.05 (dd, J=23.3, 17.2 Hz, 1H), 5.61 (dd, J=49.7, 10.5 Hz, 1H), 4.44, 4.00 (d, J=10.7 Hz, 1H), 4.30 (d, J=10.5 Hz, 1H), 4.19-4.05 (m, 3H), 3.50, 2.90 (t, J=11.0 Hz, 1H), 3.12-3.05 (m, 1H), 2.02-1.95 (m, 1H), 1.85 (d, J=12.7 Hz, 1H), 1.60-1.53 (m, 2H), 1.28-1.16 (m, 24H), 0.79 (t, J=6.9 Hz, 3H).

As detected by mass spectrometry, $[M+H]^+$=681.23, in consistence with the molecular structural formula.

Example 9 Preparation of Compound 9

The same preparation steps as in Example 1 were performed, except that the isopropyl chloroformate was replaced with crude 3-pentyl chloroformate prepared from 5 eq. of 3-pentanol, 7.5 eq. of triethylamine and 2.5 eq. of triphosgene. The reaction was subject to column chromatography, giving 1.11 g of the target compound at a yield of 17.1%.

$^1$H NMR (600 MHz, DMSO-$d_6$) δ 11.44 (s, 1H), 8.86-8.47 (m, 1H), 7.82-7.32 (m, 5H), 7.25-6.89 (m, 6H), 6.74 (ddd, J=25.8, 16.0, 10.2 Hz, 1H), 6.05 (dd, J=23.7, 17.5 Hz, 1H), 5.61 (dd, J=55.1, 10.5 Hz, 1H), 5.02-3.74 (m, 6H), 1.79-1.29 (m, 8H), 0.81 (dt, J=27.6, 7.4 Hz, 6H).

As detected by mass spectrometry, $[M+H]^+$=555.19, in consistence with the molecular structural formula.

Example 10 Preparation of Compound 10

The same preparation steps as in Example 1 were performed, except that the isopropyl chloroformate was replaced with crude 2,4-dimethyl-3-pentyl chloroformate prepared from 5 eq. of 2,4-dimethyl-3-pentanol, 7.5 eq. of triethylamine and 2.5 eq. of triphosgene. The reaction was subject to column chromatography, giving 1.07 g of the target compound at a yield of 16.3%.

$^1$H NMR (400 MHz, DMSO-$d_6$) δ 11.43 (s, 1H), 8.88 (d, J=12.4 Hz, 1H), 7.82 (d, J=8.3 Hz, 2H), 7.42-7.37 (m, 2H), 7.17-7.04 (m, 5H), 6.86-6.68 (m, 1H), 6.07 (t, J=15.8 Hz, 1H), 5.69-5.54 (m, 1H), 4.46 (d, J=5.3 Hz, 1H), 4.37-4.30 (m, 1H), 4.12 (d, J=14.2 Hz, 1H), 3.99 (dd, J=14.2, 7.1 Hz, 1H), 2.07 (dd, J=13.2, 10.0 Hz, 2H), 1.96-1.82 (m, 4H), 1.44 (s, 1H), 1.26-1.12 (m, 1H), 0.85 (d, J=6.4 Hz, 12H).

As detected by mass spectrometry, $[M+H]^+$=583.32, in consistence with the molecular structural formula.

Example 11 Preparation of Compound 11

The same preparation steps as in Example 1 were performed, except that the isopropyl chloroformate was replaced with crude n-octyl chloroformate prepared from 5 eq. of n-octanol, 7.5 eq. of triethylamine and 2.5 eq. of triphosgene. The reaction was subject to column chromatography, giving 0.57 g of the target compound at a yield of 8.4%.

$^1$H NMR (600 MHz, DMSO-$d_6$) δ 11.49 (s, 1H), 8.84 (d, J=17.2 Hz, 1H), 7.83 (d, J=7.6 Hz, 2H), 7.40 (dd, J=8.2, 7.7 Hz, 2H), 7.16 (t, J=7.4 Hz, 1H), 7.11 (t, J=9.6 Hz, 2H), 7.05 (t, J=6.6 Hz, 2H), 6.84-6.69 (m, 1H), 6.08 (dt, J=22.5, 11.3 Hz, 1H), 5.64 (dd, J=49.0, 10.3 Hz, 1H), 4.38 (d, J=85.6 Hz, 1H), 4.21-3.95 (m, 4H), 3.52, 2.92 (t, J=11.2 Hz, 1H), 3.11 (dd, J=22.3, 11.0 Hz, 1H), 2.10-1.85 (m, 4H), 1.65-1.56 (m, 2H), 1.27-1.20 (m, 10H), 0.83 (t, J=6.8 Hz, 3H).

As detected by mass spectrometry, $[M+H]^+$=597.35 and $[M+Na]^+$=619.33, in consistence with the molecular structural formula.

Example 12 Preparation of Compound 3

Similar to Example 3, butyl chloroformate was also used as a starting material. This Example differs from Example 3 essentially in the order in which the materials were added. In Example 3, the substrate and the butyl chloroformate were dissolved in the solvent, and the base was then added dropwise to initiate the reaction. In contrast, in this Example, the substrate and the base were dissolved in the solvent, and the butyl chloroformate was then added dropwise to initiate the reaction. Specifically, the following steps were performed in this Example.

To a reaction flask, 0.5 g of the substrate (1-[(3R)-3-[4-amino-3-(4-phenoxyphenyl)-1H-pyrazolo[3,4-D]pyrimidin-1-yl]-1-piperidinyl]-2-propen-1-one), 7.5 mL of the solvent (dichloromethane) and 6.0 eq. of the base (pyridine) were added. After the substrate and the base were dissolved in the solvent, a solution of 2.0 eq. of the butyl chloroformate in 1 mL of the solvent (dichloromethane) was slowly added dropwise at 0-10° C. to the reaction flask. The temperature was raised to 10-20° C., and stirring was initiated. A sample was taken and tested.

HPLC analysis revealed that the reaction contained a residue of the starting substrate (0.97%) and a disubstituted product (1.31%) of structural formula (II) below. The rest was the target product Compound 3.

(II)

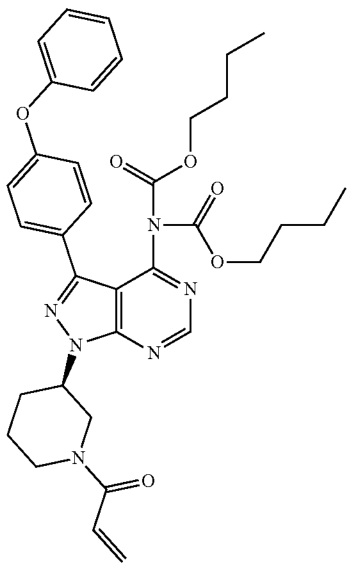

Comparative Example 1

Likewise, butyl chloroformate was chosen as a starting material. Materials were added in such a manner that, after a substrate and a base was dissolved in a solvent, the butyl chloroformate was added dropwise to trigger the reaction. Specifically, the following steps were performed in this Comparative Example.

Under the protection of nitrogen, to a 500-ml three-neck flask, 10 g of the substrate (1-[(3R)-3-[4-amino-3-(4-phenoxyphenyl)-1H-pyrazolo[3,4-D]pyrimidin-1-yl]-1-piperidinyl]-2-propen-1-one), 200 g of the solvent (dichloromethane) and 3.6 eq. (6.45 g) of the base (pyridine) were added. After the substrate and the base were dissolved in the solvent, 3.2 eq. (10 g) of the butyl chloroformate was added dropwise at 25° C. After the dropwise addition was completed, the reaction was run at room temperature for 3-4 hours.

TLC monitoring revealed that the disubstituted product of structural formula (II) predominated after 3-4 hours of reaction and that some of the starting materials remained.

Comparative Example 2

Similarly, butyl chloroformate was chosen as a starting material. Materials were added in such a manner that, after a substrate and a base was dissolved in a solvent, the butyl chloroformate was added dropwise to trigger the reaction. Specifically, the following steps were performed in this Comparative Example.

To a reaction flask, 0.5 g of the substrate (1-[(3R)-3-[4-amino-3-(4-phenoxyphenyl)-1H-pyrazolo[3,4-D]pyrimidin-1-yl]-1-piperidinyl]-2-propen-1-one), 5 mL of the solvent (dichloromethane) and 2.0 eq. of the base (triethylamine) were added. At 0-10° C., 2.0 eq. of the butyl chloroformate was slowly added dropwise. After 2 h of stirring, a sample was taken and tested.

HPLC analysis revealed that there remained large amounts of the starting materials.

Comparative Example 3

Similarly, butyl chloroformate was chosen as a starting material. Materials were added in such a manner that, after a substrate and a base was dissolved in a solvent, the butyl chloroformate was added dropwise to trigger the reaction. Specifically, the following steps were performed in this Comparative Example.

To a reaction flask, 0.5 g of the substrate (1-[(3R)-3-[4-amino-3-(4-phenoxyphenyl)-1H-pyrazolo[3,4-D]pyrimidin-1-yl]-1-piperidinyl]-2-propen-1-one), 7.5 mL of the solvent (tetrahydrofuran) and 5.0 eq. of the base (pyridine) was added. At 0-10° C., a solution of 6.0 eq. of the butyl chloroformate in 1 mL of the solvent (tetrahydrofuran) was slowly added dropwise to the reaction flask. The temperature was raised to 10-20° C., and stirring was initiated. A sample was taken and tested.

HPLC analysis showed that, in the reaction mixture, the target product compound 3 was present at 53% and the disubstituted product of structural formula (II) was present at 32%.

Comparative Example 4

Similarly, butyl chloroformate was chosen as a starting material. Materials were added in such a manner that, after a substrate and a base was dissolved in a solvent, the butyl chloroformate was added dropwise to trigger the reaction. Specifically, the following steps were performed in this Comparative Example.

To a reaction flask, 0.5 g of the substrate (1-[(3R)-3-[4-amino-3-(4-phenoxyphenyl)-1H-pyrazolo[3,4-D]pyrimidin-1-yl]-1-piperidinyl]-2-propen-1-one), 7.5 mL of the solvent (dichloromethane) and 6.0 eq. of the base (pyridine) were added. At 0-10° C., a solution of 3.0 eq. of the butyl chloroformate in 1 mL of the solvent (dichloromethane) was slowly added dropwise to the reaction flask. The temperature was raised to 10-20° C., and stirring was initiated. A sample was taken and tested.

HPLC analysis showed that, in the reaction mixture, the target product compound 3 was present at 74.4% and the disubstituted product of structural formula (II) was present at 18.6%.

According to analysis based on the above results of Example 12 and Comparative Examples 1-4, when the materials are added in such a manner that the butyl chloroformate is added dropwise after the substrate and the base are dissolved in the solvent, it is necessary to strictly control the reaction conditions, including the percentage of the added base, the percentage of the added chloroformate and the temperature at which the chloroformate is added. Reaction control under the conditions of Example 12 is favorable to the formation of the monosubstituted 4-amino target product. Otherwise, the formation of the disubstituted 4-amino impurity, or incomplete reaction of the starting materials tends to occur, making it impossible to obtain the monosubstituted 4-amino target product.

According to the results of Comparative Example 1, improper control of the percentages of the added base and chloroformate and of the temperature at which the chloroformate is added will make it impossible to produce the monosubstituted target product.

According to the results of Comparative Example 2, improper control of the percentage of the added base will make the substitution reaction difficult to occur.

According to the results of Comparative Examples 3 and 4, improper control of the percentages of the added base and chloroformate will be prone to easy formation of the disubstituted impurity at a rather percentage, which will significantly reduce the presence of the monosubstituted target product.

Example 13: Pharmacokinetic Assays of Compounds

Instruments: ultra high performance liquid chromatography (Acquity UPLC, Waters) system; triple quadrupole mass spectrometer (Qtrap 5500, Sciex); high-speed refrigerated centrifuge (5430R, Eppendorf).

Chromatography Conditions: Column: Waters BEH C18 2.1×50 mm (1.7 m); Column Temperature: 45° C.; Mobile Phase: 0.1% aqueous solution of formic acid (A)/acetonitrile; Gradient: see Table 2 below:

TABLE 2

| Gradient Table Time | Flow Rate | % A | % B |
|---|---|---|---|
| Initial | 0.400 | 70.0 | 30.0 |
| 3.00 | 0.400 | 0.0 | 100.0 |
| 3.50 | 0.400 | 0.0 | 100.0 |
| 4.00 | 0.400 | 0.0 | 100.0 |
| 4.10 | 0.400 | 70.0 | 30.0 |
| 5.10 | 0.400 | 70.0 | 30.0 |

Mass Spectrometry Condition: Mode: positive ion multiple reaction monitoring (MRM); Curtain Gas: 45 psi; Gas 1: 45 psi; Gas 2: 45 psi; Ion Source Temperature: 500° C.; Ion Source Voltage: 5000 V.

Precursor ions (Q1), product ions (Q3) and collision energy (CE) of some compounds are listed in Table 3 below.

TABLE 3

| | ID | Q1 Mass (Da) | Q3 Mass (Da) | Time (msec) | CE(volts) |
|---|---|---|---|---|---|
| 1 | 4-AAM | 441.200 | 304.100 | 100.0 | 40.000 |
| 2 | 1 | 527.200 | 441.200 | 100.0 | 35.000 |
| 3 | 2 | 527.200 | 441.200 | 100.0 | 35.000 |
| 4 | 3 | 541.300 | 441.200 | 100.0 | 40.000 |
| 5 | 4 | 541.300 | 441.200 | 100.0 | 40.000 |
| 6 | 5 | 569.300 | 441.200 | 100.0 | 40.000 |
| 7 | IS | 570.300 | 138.100 | 100.0 | 35.000 |

Experimental Animals: male SD rats, weighing 200-240 grams, fasting overnight before experiments.

Drug Preparation: 4-AAM and test compounds (Compounds 1-5) were accurately weighed according to an administration dose of 30.0 mg/kg and each dispensed in a 0.5% CMC-Na solution according to an administration volume of 2 ml/200 g, resulting in a suspension. Each suspension is prepared before administration.

Drug Administration to and Blood Collection from Animals: the drugs were oral gavage administered to the rats, and 100-1 blood samples were taken before administration and 10 min, 20 min, 40 min, 1 h, 1.5 h, 4.5 h, 7 h, 9 h, 10 h, 22 h and 24 h after administration. Each sample was placed in an ice bath, centrifuged for plasma collection, frozen and stored.

Plasma Drug Concentration Data and Calculation of Pharmacokinetic Parameters:

Plasma drug concentration data was processed using MultiQuan 3.0 (Sciex), and pharmacokinetic parameters were calculated using the DAS 2.0 software. Plasma drug concentrations were measured in ug/L.

Figure 2:
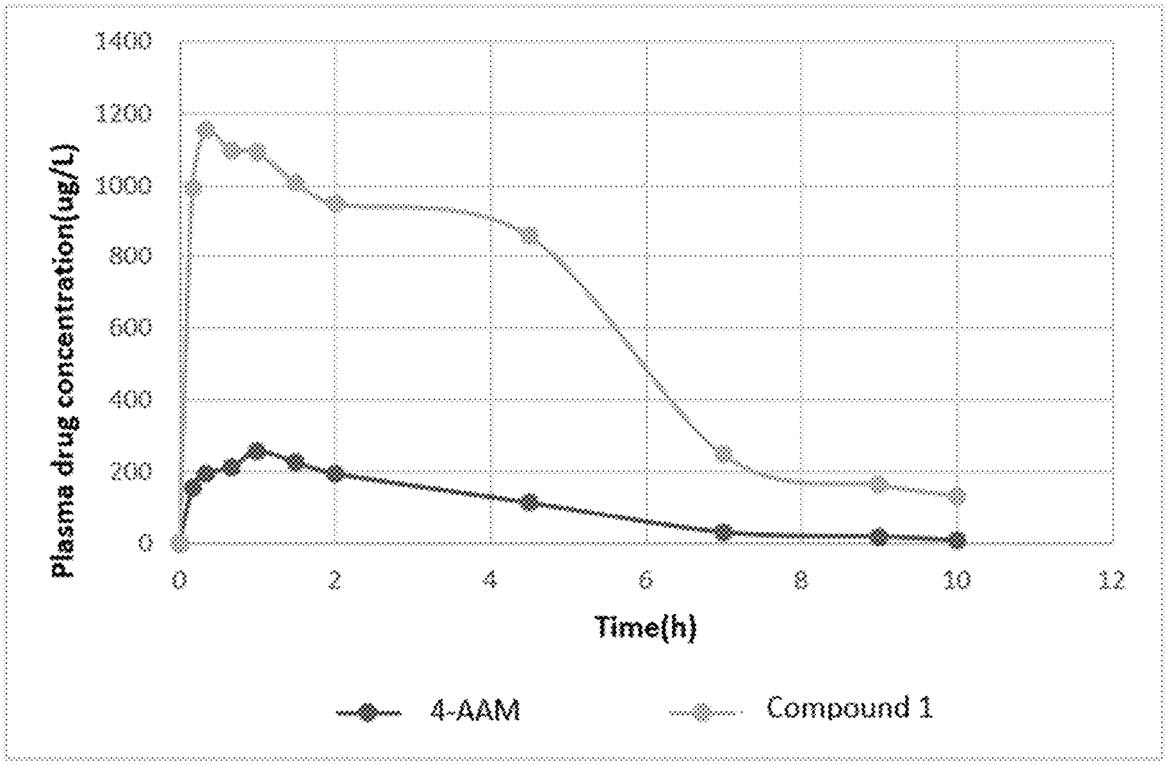
FIG. 2 shows a Plasma drug concentration-time curve of Compound 1 after it is oral gavage administered to rats.
Figure 3:
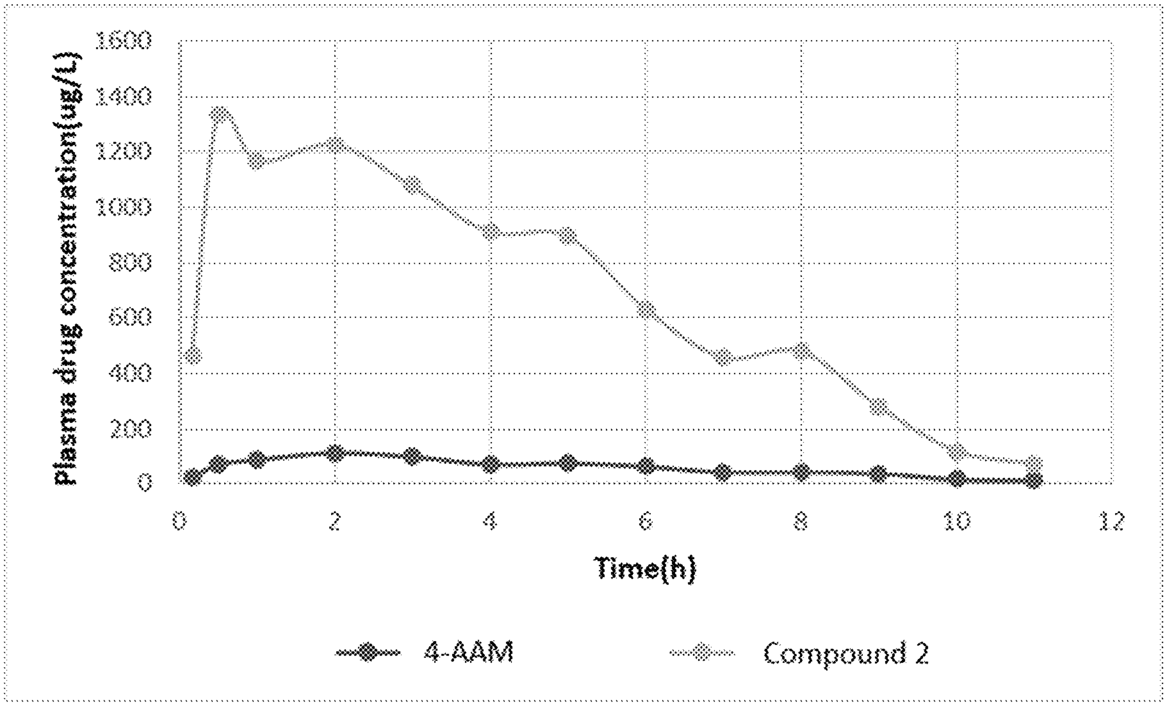
FIG. 3 shows a Plasma drug concentration-time curve of Compound 2 after it is oral gavage administered to rats.
Figure 4:
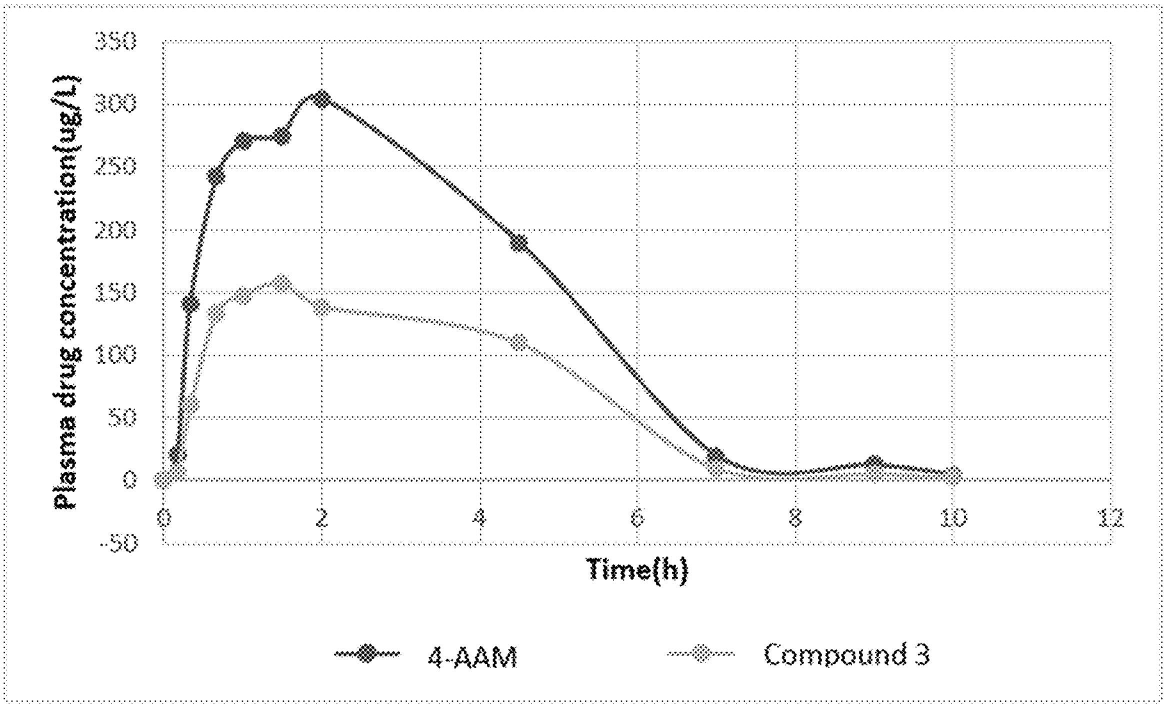
FIG. 4 shows a Plasma drug concentration-time curve of Compound 3 after it is oral gavage administered to rats.
Figure 5:
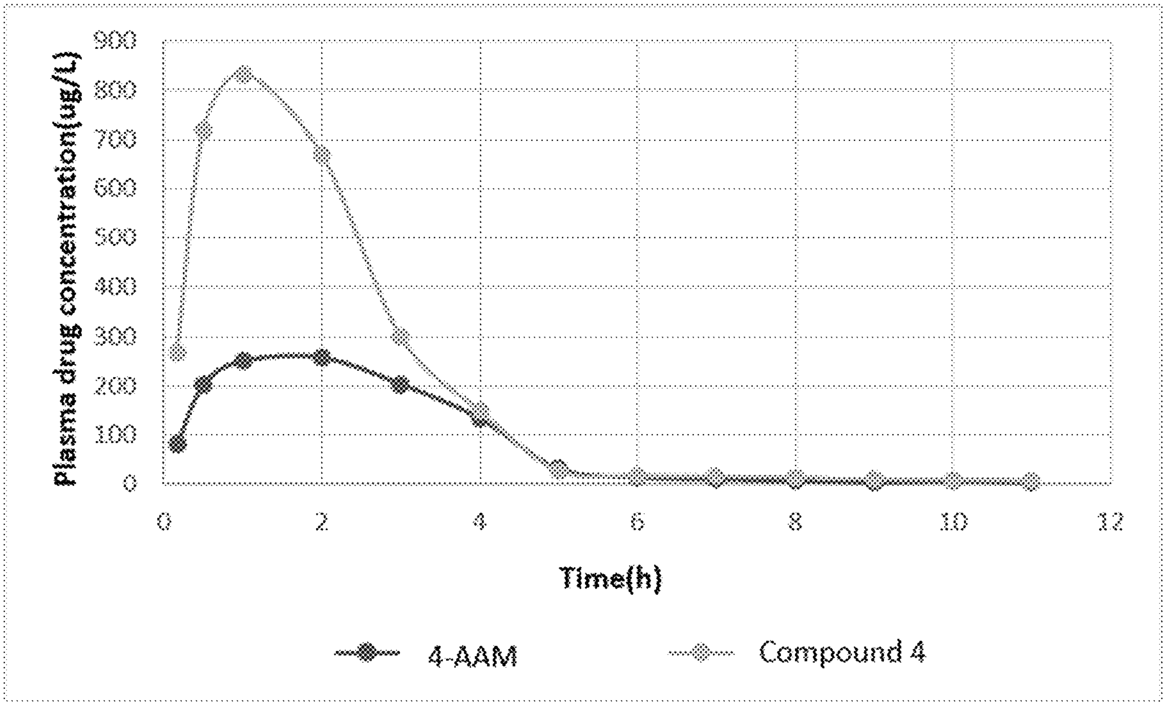
FIG. 5 shows a Plasma drug concentration-time curve of Compound 4 after it is oral gavage administered to rats.
Figure 6:
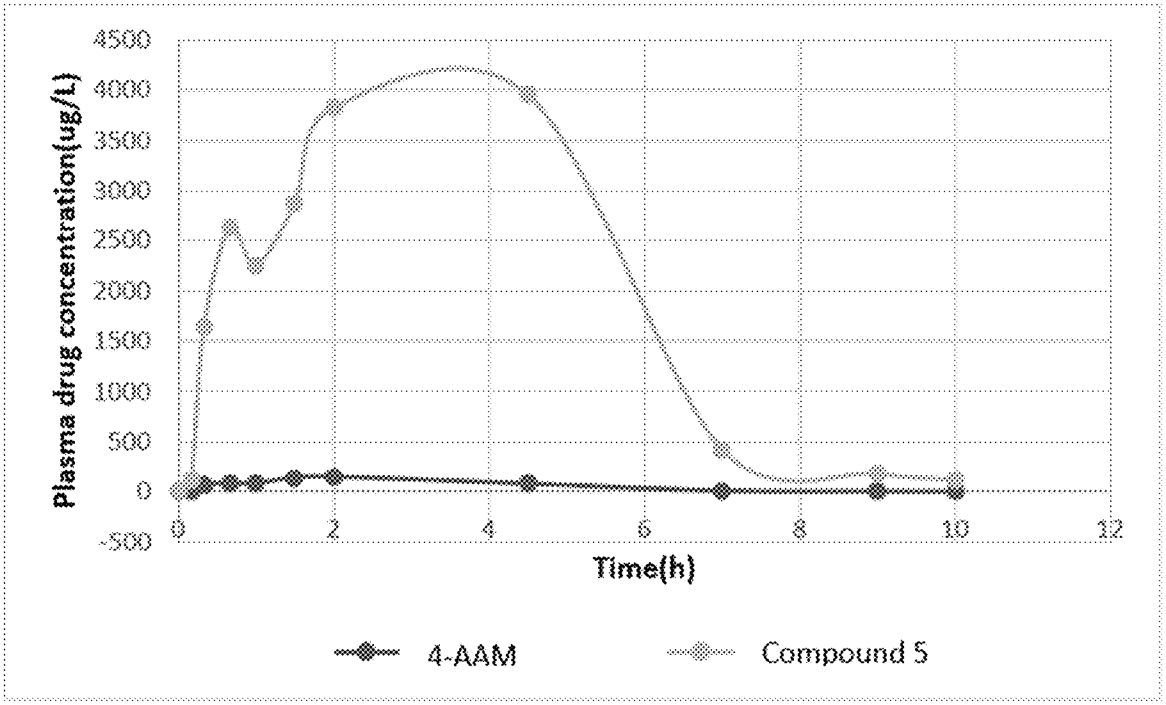
FIG. 6 shows a Plasma drug concentration-time curve of Compound 5 after it is oral gavage administered to rats.

FIGS. 1 to 6 show plasma drug concentration-time curves of respective test groups treated with 4-AAM and Compounds 1-5. Once absorbed, Compounds 1-5 can rapidly enter the blood plasma and be hydrolyzed into the 4-amino active metabolite (4-AAM) that can exert the intended therapeutic effect. Table 4 presents the results of the pharmacokinetic assays.

TABLE 4

| Parameter | Unit | 4-AAM | Compound 1 | Compound 2 | Compound 3 | Compound 4 | Compound 5 |
|---|---|---|---|---|---|---|---|
| AUC(0-t) | ug/L*h | 757.5 | 1038.6 | 663.0 | 1366.7 | 964.1 | 584.0 |
| AUC(0-∞) | ug/L*h | 822.2 | 1059.6 | 706.3 | 1375.6 | 976.4 | 587.1 |
| AUMC(0-t) | | 1316.6 | 2950.4 | 2844.3 | 3939.9 | 2405.5 | 1659.5 |
| AUMC(0-∞) | | 2805.6 | 3200.9 | 3495.04 | 4052.0 | 2586.7 | 1696.7 |
| MRT(0-t) | h | 1.7 | 2.8 | 4.29 | 2.9 | 2.5 | 2.8 |
| MRT(0-∞) | h | 3.4 | 3.0 | 4.9 | 2.9 | 2.6 | 2.9 |
| VRT(0-t) | h^2 | 2.0 | 4.6 | 7.2 | 3.3 | 2.9 | 3.0 |
| VRT(0-∞) | h^2 | 47.6 | 6.3 | 13.5 | 3.8 | 4.8 | 3.5 |
| t½z | h | 8.9 | 1.7 | 2.338 | 1.3 | 2.5 | 1.3 |
| Tmax | h | 1.5 | 1.0 | 2.0 | 2.0 | 2.0 | 2.0 |
| CLz/F | L/h/kg | 36.5 | 28.3 | 42.5 | 21.8 | 30.7 | 51.1 |
| Vz/F | L/kg | 470.6 | 71.3 | 143.3 | 42.0 | 109.1 | 92.6 |
| Cmax | ug/L | 312.0 | 257.2 | 111.0 | 304.4 | 256.7 | 143.9 |

As can be seen from FIGS. 1 to 6 and from the results of the pharmacokinetic assays in Table 4, the compounds of the present invention underwent a mild first-pass effect and delivered the intended therapeutic effect after being oral absorbed. Compared with 4-AAM administered at the same molar amount, Compounds 1, 3 and 4 had a much greater AUC. Moreover, the compounds of the present invention had a lower peak plasma drug concentration, a prolonged time to peak concentration and a longer mean retention time, indicating that their pharmacokinetic properties that can better address clinical needs.

Compound 3 was hydrolyzed at the highest rate, and the resulting 4-AAM had both a greater AUC and a higher plasma drug concentration than Compound 3 itself. The AUC was 180% of that of 4-AAM directly administered at the same molar amount. Its time to peak concentration was 2 h, and its mean retention time was 2.9 h.

Compound 1 had an AUC, which was 137% of that of 4-AAM administered at the same molar amount, a time to peak concentration of 1 h and a mean retention time of 2.8 h. Compound 4 had an AUC, which was 127% of that of 4-AAM administered at the same molar amount, a time to peak concentration of 2 h and a mean retention time of 2.5 h. Compound 2 had an AUC, which was 88% of that of 4-AAM administered at the same molar amount, a time to peak concentration of 2 h and a mean retention time of 4.3 h.

The compounds of the present invention can provide higher bioavailability, a more constant plasma drug concentration profile and a long duration of action. They are significantly improved over the existing drugs.

The invention claimed is:

1. A pyrazolopyrimidine ester compound, characterized in being of the following general structural formula:

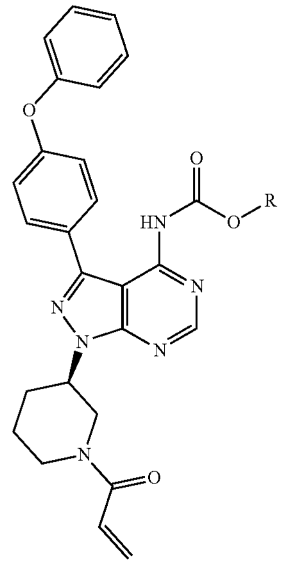

where R is —$(CH_2)_3CH_3$, and the ester group is monosubstituted on the 4-amino group of the pyrazolo[3,4-D]pyrimidine ring.

2. A method of preparation of the pyrazolopyrimidine ester compound according to claim 1, characterized in taking 1-[(3R)-3-[4-amino-3-(4-phenoxyphenyl)-1H-pyrazolo[3,4-D]pyrimidin-1-yl]-1-piperidinyl]-2-propen-1-one as a starting material and obtaining a target compound from its reaction with n-butyl chloroformate, which is represented by the following equation:

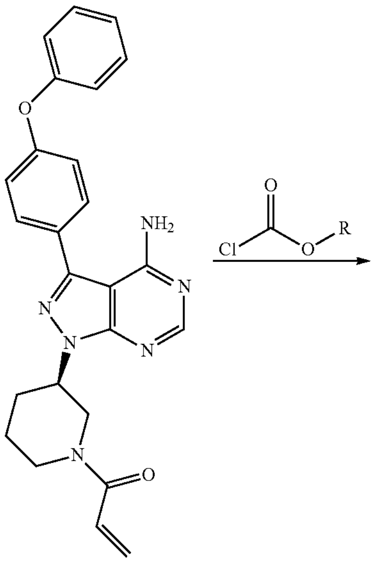

-continued

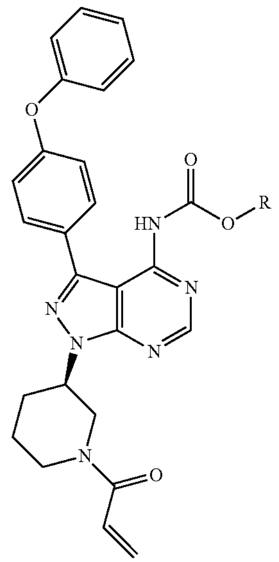

where R is —$(CH_2)_3CH_3$, and the target compound is a monoester substituted at the 4-amino group of the pyrazolo[3,4-D]pyrimidine ring.

3. The method of preparation according to claim 2, characterized in comprising the steps of:

adding the starting material 1-[(3R)-3-[4-amino-3-(4-phenoxyphenyl)-1H-pyrazolo[3,4-D]pyrimidin-1-yl]-1-piperidinyl]-2-propen-1-one, the chloroformate and a solvent to a reactor; and after the starting material and the chloroformate are dissolved in the solvent, adding a base to trigger the reaction.

4. The method of preparation according to claim 2, characterized in comprising the steps of:

adding the starting material 1-[(3R)-3-[4-amino-3-(4-phenoxyphenyl)-1H-pyrazolo[3,4-D]pyrimidin-1-yl]-1-piperidinyl]-2-propen-1-one, a solvent and a base to a reactor; and after the starting material and the base are dissolved in the solvent, adding the chloroformate to trigger the reaction, wherein with the starting material being taken as a reference, the base is added at an amount of 6.0±0.5 eq. and the chloroformate is added at an amount of 2.0±0.5 eq., and wherein the chloroformate is added, after being dissolved in the solvent, at 0-10° C. to trigger the reaction.

5. A method for treating lymphoma or lymphocytic leukemia, comprising orally administering a therapeutically effective amount of the compound of claim 1 to a human subject in need thereof.

* * * * *